(12) United States Patent
Vertelova et al.

(10) Patent No.: US 11,286,171 B2
(45) Date of Patent: Mar. 29, 2022

(54) THERAPEUTIC METALLIC NANOPARTICLE COMPOSITION AND METHOD OF USE AND MANUFACTURE THEREOF

(71) Applicants: Regina Vertelova, San Diego, CA (US); Nikolai Tankovich, San Diego, CA (US)

(72) Inventors: Regina Vertelova, San Diego, CA (US); Nikolai Tankovich, San Diego, CA (US)

( * ) Notice: Subject to any disclaimer, the term of this patent is extended or adjusted under 35 U.S.C. 154(b) by 0 days.

(21) Appl. No.: 17/086,374

(22) Filed: Oct. 31, 2020

(65) Prior Publication Data
US 2021/0130182 A1 May 6, 2021

Related U.S. Application Data

(60) Provisional application No. 62/979,562, filed on Feb. 21, 2020, provisional application No. 62/929,241, filed on Nov. 1, 2019.

(51) Int. Cl.
| | |
|---|---|
| *C01G 5/00* | (2006.01) |
| *C07H 15/252* | (2006.01) |
| *C07C 279/26* | (2006.01) |
| *C01G 7/00* | (2006.01) |
| *C01G 55/00* | (2006.01) |
| *A61K 47/69* | (2017.01) |
| *B82Y 40/00* | (2011.01) |
| *B82Y 5/00* | (2011.01) |

(52) U.S. Cl.
CPC ............ *C01G 5/00* (2013.01); *A61K 47/6903* (2017.08); *C01G 7/00* (2013.01); *C01G 55/00* (2013.01); *C07C 279/26* (2013.01); *C07H 15/252* (2013.01); *B82Y 5/00* (2013.01); *B82Y 40/00* (2013.01)

(58) Field of Classification Search
CPC . C01G 5/00; C01G 7/00; C01G 55/00; C07H 15/252; C01C 279/26; A61K 47/6903; B82Y 40/00; B82Y 5/00
See application file for complete search history.

(56) References Cited

FOREIGN PATENT DOCUMENTS

| | | |
|---|---|---|
| CN | 109570488 A1 | 4/2019 |
| RU | 2419439 B1 | 5/2011 |
| RU | 2640277 B1 | 12/2017 |

OTHER PUBLICATIONS

Banu et al, Doxorubicin loaded polymeric gold nanoparticles targeted to humanfolate receptor upon laser photothermal therapy potentiates chemotherapy in breast cancer cell lines, Journal of Photochemistry and Photobiology B, vol. 149, pp. 116-128 (Year: 2015).*

(Continued)

*Primary Examiner* — Carlos A Azpuru
(74) *Attorney, Agent, or Firm* — TMB Law; Timothy M. Brown

(57) ABSTRACT

The invention is directed to a composition of metal particles and methods of manufacturing and using the composition in the treatment of microbial infections and cancer. The particles can be nanoparticles having coupled thereto at least one of a surfactant, an antibiotic, and a drug. The particles of the invention achieve enhanced stability, enhanced cytotoxicity, and enhanced antimicrobial activity through novel combinations of metals, surfactants, antibiotics, and drugs.

34 Claims, 7 Drawing Sheets

(56) References Cited

OTHER PUBLICATIONS

Rodriguez-Gonzalez et al, Multishell bimetallic AuAg nanoparticles: synthesis, structure and optical properties , J. Mater. Chem. 15, 1755-1759 (Year: 2005).*
Tabaran et al, Silver Nanoparticles for the Therapy of Tuberculosis, Nanoparticles for the Therapy of Tuberculosis. Int J Nanomedicine;15:2231-2258 https://doi.org/10.2147/IJN.S241183 (Year: 2005).*
International Search Report and Written Opinion; International Application No. PCT/US2020/058446.
Krutyakov et al.; Benzyldimethyl[3-(miristoylamino)-proplyl] ammonium chloride stabilized silver nanoparticles in medicine: reults of clinical trials for treatment of infectious diseases of dogs and perspectives for humans; Eur. J. Nanomed. 2016: 8(4): 185-194.
Cameron et al.; A Current Overview of the Biological and Cellular Effects of Nanosilver; Int. J. Mol. Sci. 2018, 19, 2030.

* cited by examiner

THERAPEUTIC METALLIC NANOPARTICLE COMPOSITION AND METHOD OF USE AND MANUFACTURE THEREOF

CROSS-REFERENCE TO RELATED APPLICATIONS

This application claims the benefit of U.S. Provisional Application Nos. 62/929,241 filed Nov. 1, 2019 and 62/979,562 filed Feb. 21, 2020, the entire contents of which are incorporated herein by reference for all purposes.

FIELD OF INVENTION

The invention generally relates to nanotechnology. More particularly, the invention relates to a cytotoxic, antimicrobial nanoparticle composition and methods of its use and manufacture in therapeutic, antiseptic, and other applications.

BACKGROUND

Spread of harmful bacteria, fungi, viral infections and cancer are among the utmost challenges humanity faces on daily basis. More and more drug- and multidrug-resistant bacterial pathogens are identified by the scientific community every year. In 2014, the World Health Organization (WHO) warned that humanity is approaching the post-antibiotic era; a world in which antibiotics will no longer be effective, and even minute contaminations will be life threatening.

Small silver nanoparticles, the size of proteins, are known to corrode and dissolve in vivo yielding Ag+ ions that induce reactive oxygen species (ROS) and interfere with respiration mechanisms of bacteria resulting in a very broad-spectrum antibiotic. Silver nanoparticles have received significant attention as powerful antimicrobial and neoplastic agents resulting from their high surface-to-volume ratios and their unique physical and chemical properties [11-13]. Silver nanoparticles have been demonstrated to act as effective antibacterial agents against various multidrug-resistant bacteria like MRSA and methicillin-resistant *S. epidermidis* bacteria [14]. However, silver nanoparticles have relatively low stability in air and their size and shape are difficult to control in an aqueous environment. Moreover, silver nanoparticle preparations require concentrated solutions to be effective [15].

Chemotherapeutic drugs containing platinum are first- and second-line therapy for many types of cancer. Cisplatin, for example, is used in testicular, ovarian, lung, and head and neck cancer [16]. Cisplatin's clinical use, however, is aggravated with systemic toxicity, primarily to the kidneys [17]. A series of improved analogues have been developed since Cisplatin was approved by the FDA in 1978. Still, the main limitation to the clinical usefulness of Cisplatin (and its modifications) as anticancer drugs is the high incidence of chemoresistance [18]. Generally, cancer therapies based on a single drug are infective due to the complex microenvironment of cancer cells and drug resistance mechanisms [19]. Also, the use of chemotherapeutic drugs increases the risk of infections. Thus, there is a need for agents that have both antibacterial and anticancer effects against drug-resistant cancer cells.

What is needed in the art therefor is an improved cytotoxic, antimicrobial nanoparticle therapeutic with improved stability, consistency, and greater potency against drug resistant infections and cancers.

SUMMARY OF THE INVENTION

The invention provides a nanoparticle composition having synergistically enhanced stability and efficacy in the treatment of drug-resistant infections and tumors. The invention achieves this and other objectives by providing unique combinations of metals, surfactants, antibiotics, and drugs.

It is therefore an object of the invention to provide a composition comprising (i) particles of at least one metal, and (ii) at least one surfactant.

In some aspects, the metal is a noble metal.

In some aspects, the metal is selected from the group consisting of silver, gold, platinum, palladium, osmium, iridium, rhodium, ruthenium, and combinations thereof.

In some aspects, the particles include monometallic particles, polymetallic particles, or a combination thereof.

In some aspects, the particles include bimetallic particles.

In some aspects, the bimetallic particles are silver and gold bimetallic particles, silver and platinum bimetallic particles, or a combination thereof.

In some aspects, the composition comprises about 99.67% molar silver, about 99.50% molar silver, about 97.50% molar silver, about 70% molar silver, or about 50% molar silver.

In some aspects, the particles are polymetallic particles having a core of a first one or more metals, and a shell of a second one or more metals.

In some aspects, the particles are bimetallic particles having a core of gold or platinum and a shell of silver.

In some aspects, the particles are polymetallic particles having a structure selected from an alloy, a mixed alloy, a subcluster with two or more interfaces, and combinations thereof.

In some aspects, the subclusters are segregated subclusters, mixed subclusters, or a combination thereof.

In some aspects, the alloy is an intermetallic alloy.

In some aspects, the composition comprises silver monometallic particles, gold monometallic particles, platinum monometallic particles, or combinations thereof.

In some aspects, the particles are nanoparticles.

In some aspects, the nanoparticles have a mean diameter that is between about 5 nanometers and about 30 nanometers, or between about 5 nanometers and about 400 nanometers.

In some aspects, the particles have a shape that is substantially spherical, substantially oval, or substantially cuboidal.

In some aspects, the surfactant is selected from one or more of a cationic surfactant, an anionic surfactant, an amphoteric surfactant, and a charge-neutral surfactant.

In some aspects, the surfactant is selected from one or more of benzyl-dimethyl-[3-(tetradecanoylamino)propyl] ammonium chloride, a cetyltrimethylammonium salt, a benzalkonium salt, didecyldimethylammonium chloride, octenidine dihydrochloride, dimethyl benzyl ammonium chloride, a polyhexamethylene biguanide, a polyhexamethylene guanidine, a polyhexamethylene biguanide salt, a polyhexamethylene guanidine salt, sodium lauryl ether sulfate, and sodium cocaminopropionate.

In some aspects, the surfactant is coupled to the surface of the particles.

In some aspects, the composition further comprises an antibiotic.

In some aspects, the antibiotic is at least one of tetracycline and vancomycin.

In some aspects, the antibiotic is coupled to the surface of the particles, coupled to the surfactant, or a combination thereof.

In some aspects, the composition further comprises a drug.

In some aspects, the drug is chemotherapeutic cancer drug.

In some aspects, the drug is one or more of doxorubicin, glucosamine, and metformin.

In some aspects, at least a portion of the drug molecules are coupled to the surface of the particles, coupled to the surfactant, coupled to the antibiotic, or combinations thereof.

In some aspects, the composition further comprises at least one of a carrier and an excipient, wherein at least a portion of one or more of the surfactant, the antibiotic, and the drug is dissolved in or suspended in the carrier and excipient.

In some aspects, the composition is a colloid.

In some aspects, the composition is in a form selected from a liquid, gel, sol, and foam.

In some aspects, the composition is in an administration form selected from a pill, capsule, tablet, microbead, injection, infusion, and suppository.

In some aspects, the composition is in contact with a bandage or wound dressing.

In some aspects, the composition is in contact with a textile, such as a bed sheet, blanket, pillow, pillow case, seat cover, table cover, door mat, gauze, surgical mask, surgical gown, patient gown, menstrual pad, or tampon.

In some aspects, the invention provides a method of preventing or inhibiting microbial growth on or in a material, comprising contacting the material with the composition.

In some aspects, the invention provides a method of treating a microbial infection, comprising administering the composition to a patient in need thereof.

In some aspects, the patient has at least one of a bacterial infection, viral infection, and a fungal infection.

In some aspects, the invention provides a method of treating cancer comprising administering the composition to a patient in need thereof.

BRIEF DESCRIPTION OF THE DRAWINGS

FIGS. 8A-8C show nanoparticle size distribution of the nanoparticles of Example 7, wherein FIG. 8A shows size distribution for Sample 4-1, FIG. 8B shows size distribution for Sample 4-2, and FIG. 8C shows size distribution for Sample 4-3.

FIGS. 10A-10C show TEM images of the nanoparticles of Examples 10 and 11, wherein FIG. 10A represents Sample 6-1, FIG. 10B represents Sample 6-2, and FIG. 10C represents Sample 7-1.

FIGS. 11A-11C show the size distribution of the nanoparticles of Examples 10 and 11, wherein FIG. 11A represents Sample 6-1, FIG. 11B represents Sample 6-2, and FIG. 11C represents Sample 7-2.

DEFINITIONS

Figure 1:
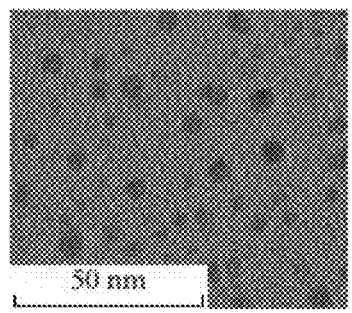
FIG. 1 is an electron micrograph of silver nanoparticles from Sample 1-1.

As used herein, the term "about" refers to the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

The terms "a" and "an," when used in conjunction with the word "comprising" in the claims or specification, denotes one or more, unless specifically noted.

The terms "is" and "are," when used in conjunction with a group of different possibilities for a limitation or element in the claims or specification, indicates the group includes, but is not limited to, the listed possibilities unless expressly specified otherwise.

As used herein, the term "metal" refers to any transition metal, including, without limitation, the noble metals. The metal can be an elemental metal, metal ion, or metal salt.

As used herein, the term "monometallic" refers to a single metal.

As used herein, the term "polymetallic" refers to a combination of two, three, four, five, or more metals.

As used herein, the term "bimetallic" refers to a combination of just two metals.

As used herein, the term "surfactant" refers to a compound that lowers the surface tension between two liquids, between a gas and a liquid, or between a liquid and a solid.

Where this disclosure refers to two or more possible limitations or elements in the alternative, such as by use of the term "or," it is contemplated that one or more of the listed limitations or elements can be specifically excluded from the embodiment that is being described.

DETAILED DESCRIPTION

The inventors surprisingly discovered that the stability of metal particles and their cytotoxic, antimicrobial effects, can be synergistically increased through unique combinations of the metals that are used, as well as their combination with one or more of a surfactant, antibiotic, and drug.

In some embodiments, the invention provides a composition comprising particles of at least one transition metal and one or more surfactants. In some non-limiting embodiments, the transition metal is a noble metal. The noble metal can be one or more of silver, gold, platinum, palladium, osmium, iridium, rhodium, and ruthenium. In other non-limiting embodiments, the metal is one or more of silver, gold, platinum, palladium, osmium, iridium, rhodium, ruthenium, copper, chromium, and iron. The particles can be monometallic, bimetallic, or polymetallic with three or more metals, or mixtures of such particles. The composition can comprise a combination of monometallic particles of different metals. For example, the composition can comprise a combination of silver particles and gold particles. Similarly, the composition can comprise monometallic particles in combination with polymetallic particles. For example, the composition can comprise monometallic silver particles, monometallic gold particles, and bimetallic silver and gold particles. In a non-limiting embodiment, the composition comprises bimetallic particles wherein the particles are gold and silver, silver and platinum, gold and platinum, or combinations thereof.

When the composition comprises particles of more than one metal, whether as polymetallic and/or monometallic particles, the composition can be formulated to contain a specific molar percentage of the metals. The molar percentage of a metal in the composition can be determined by dividing the number of mols of the metal being quantified, by the total number of mols of all metals that are present in the composition, it being understood that the molar percentages are quantified based on the amounts elemental metal and metal ions present in the composition. A molar percentage can be expressed as one or a combination of metals. In a non-limiting embodiment, the composition can be formulated to contain a first one or more metals in a molar percentage of about 1%, about 5%, about 10%, about 20%, about 30%, about 40%, or about 50%, with the second one or more metals making up the remainder of the molar percentage. For example, and by no way of limitation, the composition can be formulated to contain about 1% molar gold and about 99% molar silver, about 5% molar gold and about 95% molar silver, about 10% molar gold and about 90% molar silver, about 20% molar gold and about 80% molar silver, about 30% molar gold and about 70% molar silver, about 40% molar gold and about 60% molar silver, or about 50% molar gold and about 50% molar silver. The molar percentages disclosed herein can refer to the molar percentage of the metals in the form of particles, with or without any metal ions that may be present in the composition as a solute or salt.

Figure 6:
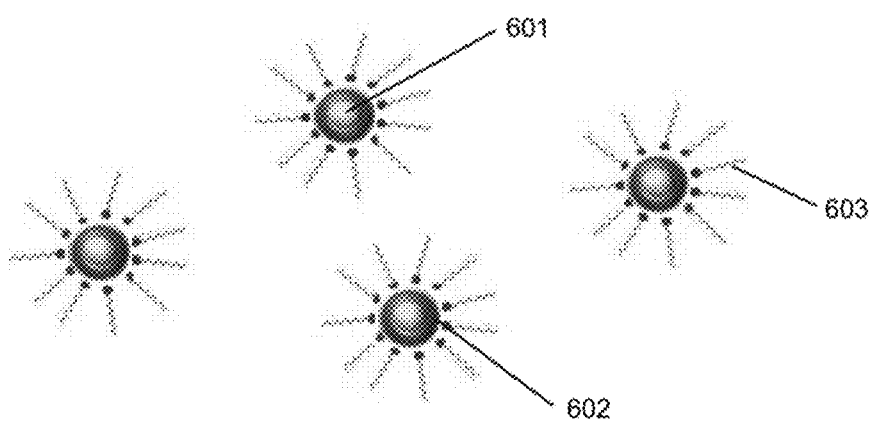
FIG. 6 is a schematic diagram of bimetallic nanoparticles having a gold core and a silver shell with a surfactant on the surface of the shell.

Particles of the composition can have a shape that is substantially spherical, substantially cuboidal, or substantially oval. The particles of the composition can have the same shape, or a mixture of shapes. For example, the composition can comprise a first portion of particles that is substantially spherical, and a second portion of particles that is substantially oval. As used herein, the term "substantially" can refer to the shape that is referenced, or that resembles the shape that is referenced. The particles can also assume a variety of structures. The structure of the particles can be a core and shell structure, an alloy (e.g. mixed alloy), or a subcluster. The particles of the composition can have the same shape, or comprise a mixture of particles of different shapes. The core and shell structure can comprise a core of a first one or more metals that is surrounded by one or more shells made from a second one or more metals. Alloy particles for use with the invention can be an intermetallic alloy. Subclusters for use with the invention can be segregated subclusters, mixed subclusters, or subclusters with one or more interfaces. The composition can comprise one of these types of subclusters, or a mixture of these subclusters. The particles can have a structure as disclosed in the following publication, the entire contents of which are incorporated herein for all purposes: Srinoi, *Appl. Sci.* 2018, 8, 1106. Core shell structures can be a core of a first one or more noble metals and at least one shell of a second one or more noble metals. FIG. 6 shows a non-limiting embodiment of bimetallic particles that have gold core 601 surrounded by a silver shell 602 with surfactant molecules 603 coupled to silver shell 602.

In some embodiments, at least a portion of the particles in the composition are nanoparticles. The nanoparticles can have a mean size that ranges between about 2 nanometers and about 15 nanometers, between about 5 nanometers and about 30 nanometers, or between about 2 nanometers and about 400 nanometers. The nanoparticles can have a mean size of up to about 15 nanometers, up to about 30 nanometers, or up to about 400 nanometers.

In some embodiments, the composition comprises one or more surfactants. Surfactants can be present in the composition in an amount that is between about 0.001 w/w % and about 0.10 w/w %, or between about 0.00001 w/w % and about 5-10 w/w %. Surfactants in the composition can be present in an amount that is between about 0.1 ppm and about 10,000 ppm, or between about 10 ppm and about 1,000 ppm. The surfactant can be one or more surfactants selected from a cationic surfactant, an anionic surfactant, an amphoteric surfactant, and a charge-neutral surfactant. Non-limiting examples of suitable surfactants include: benzyl-dimethyl-[3-(tetradecanoylamino)propyl]ammonium chloride (Miramistin®); cetyltrimethylammonium salts; benzalkonium salts (such as benzalkonium chloride); didecyldimethylammonium chloride; octenidine dihydrochloride; dimethyl benzyl ammonium chloride; polyhexamethylene guanidine; polyhexamethylene guanidine salt; polyhexamethylene biguanide; polyhexamethylene biguanide salt (such as polyhexamethylene biguanide chloride); sodium lauryl ether sulfate; and sodium cocaminopropionate. The composition can comprise just one surfactant or a combination of surfactants. Without being limited to any particular theory, mechanism, or effect, the combination of the metal particles with a surfactant inhibits oxidation of the metals in the particles thereby increasing their stability and preserving their efficacy. Moreover, and without being limited to any particular theory mechanism, or effect, combining the particles with a surfactant increases homogeneity of the shape and size of the particles, inhibits particle aggregation, stabilizes the net charge of the particles, and improves their dispersity when suspended in a medium.

The surfactant can be coupled to the surface of the particles. The surfactant can be coupled to the surface of the particles by at least one of ionic bonding, hydrogen bonding, dipole-dipole interaction, covalent bonding, and donor-acceptor interaction.

In some embodiments, the composition further comprises at least one of an antibiotic and a drug. The antibiotic and drug can be present in an amount that is between about 0.000001 w/w % and about 1-5 w/w %, or between about 0.0001 and about 0.01 w/w %. In some non-limiting embodiments, the ratio of the surfactant to the antibiotics and/or drugs is between about 2:1 and about 10:1. The ratio of the surfactant to the antibiotics and/or drugs can about 2;1, about 3:1, about 4:1, about 5:1, about 6:1, about 7:1, about 8:1, about 9:1, or about 10:1. The antibiotic and/or drugs can be present in an amount that is between about 0.01 ppm and about 2 ppm, or between about 0.1 ppm and about 0.5 ppm. The antibiotic can be, without limitation, one or more of tetracycline, vancomycin, β-lactams (including ampicillin, amoxicillin, penicillin, methicillin etc.), quinolones (enoxacin, ofloxacin, norfloxacin, ciprofloxacin etc.), aminoglicosides (kanamycin A, amikacin, tobramycin, etc.), tetracycline type (tetracycline, chlortetracycline, oxytetracycline, etc.), glycopeptide antibiotics (vancomycin, teicoplanin, telavancin, etc.), anthracycline type (doxorubicin, daunorubicin, epirubicin, idarubicin etc.) and other classes of antibiotics, bioactive amines, and aromatic compounds. In some aspects, the drug is a cancer drug Non-limiting examples of drugs for use with the invention include one or more of doxorubicin, glucosamine, and metformin. The antibiotic and/or drug can be in contact with at least one of the surface of the particles and the surfactant. The antibiotic and/or drug can be coupled to the surface of the particles, the surfactant, and/or one another by ionic bonding, hydrogen bonding, dipole-dipole interaction, covalent bonding, donor-acceptor interaction, or combinations thereof. In some embodiments, the drug is in present in the composition as a solution or suspension.

In at least one embodiment, the composition comprises a colloid wherein the particles are suspended in a medium, such as a liquid, gel, or sol. The surface of the particles in the colloid can be in contact with or coupled to one or more surfactants, one or more antibiotics, one or more drugs, or a combination thereof. At least a portion of at least one of the surfactant, antibiotic, and drug can be free of contact with the surface of the particles and independently suspended or dissolved within the medium. Without being limited to any particular theory, mechanism or effect, contacting or coupling the surfactant with the surface of the particles increases colloidal stability of the composition. The colloid can contain a dispersed phase comprising the particles in contact with or coupled to at least one of a surfactant, antibiotic, and drug, and a continuous phase comprising the medium.

In one non-limiting embodiment, the invention provides a chemotherapeutic composition of polymetallic nanoparticles having a core of a first one or more noble metals, at least one shell of a second one or more noble metals substantially surrounding the core, and at least one surfactant on the surface of the outermost shell of the nanoparticles.

In at least one embodiment, the composition is a stable suspension of colloidal silver-gold stabilized with a surfactant. The silver content in the composition can be between about 0.00001 w/w % and about 5-10 w/w %. The gold content in the composition can be between about 0.00001 w/w % and about 5-10 w/w %. The total content of the surfactants in the composition can be between about 0.00001 w/w % and about 5-10 w/w %. In at least some embodiments, the composition comprises between about 0.001 w/w % and about 0.10 w/w % of least one metal, and between about 0.001 w/w % and about 0.10 w/w % of at least one surfactant.

Metal particles can be produced by reduction methods known in the art. The following reducing agents can be used in the manufacture metal particles: sodium borohydride, citric acid, salts of citric acid (citrate), ascorbic acid, glucose, or combinations thereof.

In at least some embodiments, the composition is formulated to be administered to a patient. The composition can be formulated with a pharmaceutically acceptable excipient, pharmaceutically acceptable carrier, or combination thereof. Suitable excipients and carriers for use with the invention include, but are not limited to, those disclosed in the following references, the entire contents of which are incorporated herein by reference for all purposes: The Science and Practice of Pharmacy, $19^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The composition can assume a dosage form suitable for administration to a patient, including, but not limited to, a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, beadlet, gummy, gel, sol, injection, or combinations thereof.

In at least one aspect, the invention provides a drug delivery platform wherein nanoparticles comprising one or more metals and a surfactant enhance the delivery drugs and antibiotics into cells and microbes. Without being limited to any particular theory or mechanism, the surfactant on the surface of the nanoparticle facilitates permeation of cell membranes such that nanoparticles bearing drugs and antibiotics are permitted to enter cells and microbes with greater efficiency thereby increasing the intracellular concentration of the therapeutic. In the case of cells, the acidic environment of intracellular lysosomes liberate metal ions from the nanoparticles to permit the ions to exert a cytotoxic effect.

In some aspects, the invention provides a method of antisepsis, comprising contacting a microbe with a composition as disclosed herein. As used herein, the terms "microbe," "microbial," and the like refer, to bacteria, fungi, algae, parasite, and viruses. The microbe can be on or in a material where microbial antisepsis is desired. In other aspects, the invention provides a method for preventing or inhibiting microbial growth on or in a material, comprising contacting the material with a composition as disclosed herein. In both methods, the material can be a surface, such as the surface of a table or shelve, flooring, wall, a mat, a textile, a medical or surgical device, an appliance, a storage device, a container, a bandage or a wound dressing, for example. The material can be water, such swimming pool water, water in agricultural and aquaculture ponds applications, river water, lake water, reservoir water, or water in water treatment facility applications. The composition can be contacted with water to prevent or inhibit the growth of algae in the water.

In at least one embodiment, the invention provides a method for treating a microbial infection, comprising administering to a patient in need thereof a composition as disclosed herein. In other embodiments, the invention provides a method of treating cancer, comprising administering to a patient in need thereof a composition as disclosed herein. The cancer can be gliobastoma or ovarian cancer. In both methods of treatment, the patient can be a human. The patient can be an animal, including, without limitation, dogs, cats, cattle, horses, sheep, goats, chicken, turkeys, rats, mice, and primates. In both methods of treatment, the composition can be administered systemically or locally. The composition can be administered orally, parenterally, or a combination thereof. The composition can be administered intravenously, intraarterially, sublingually, intravaginally, rectally, topically, sub-dermally, intramuscularly, intranasally, intraocularly, intra-aurally, or combinations thereof.

The invention is demonstrated by the following examples, it being understood that the examples are merely illustrative and are not intended to limit the scope of the present invention as one skilled in the art will appreciate that variations may be possible based on the teachings of the specification herein.

EXAMPLES

The following examples exemplify some, but not necessarily all, of the various embodiments of the invention. The following examples are provided purely for illustrative purposes and do not in any way limit the scope of the present invention, it being understood that the scope of the invention is set forth in the claims and their equivalents.

Example 1

Nanoparticle Preparation—Bimetallic Nanoparticle Composition Having Miramistin®

A composition of silver and gold bimetallic nanoparticles with (Miramistin®) was prepared as follows: aqueous solutions of silver and gold salts were added to a solution of at least one surfactant under vigorous stirring, then a reducing agent was added. The reaction was carried out in an inert atmosphere of nitrogen or argon. Silver nitrate or silver acetate can be used as the silver salt, and hydrogen tetrachloroaurate as a source of gold.

The following procedure was used for the preparation of Sample 1-2. Samples 1-3 and 1-4 were prepared according to the same procedure, with adjustments made to the amounts of the metal-bearing components to achieve the molar percentages of the respective samples. Distilled water was repeatedly distilled in the atmosphere of nitrogen gas to achieve de-oxygenation. The de-oxygenized water was used for all further preparations. Aqueous solutions of 20 mg silver nitrate and 0.15 mg hydrogen tetrachloroaurate in 10 mL water were added dropwise to vigorously stirred 150 mL 0.01 w/v % benzyl-dimethyl-[3-(tetradecanoylamino)propyl]ammonium chloride (Miramistin®) in water. The resulting mixture was stirred for 15 min, followed by dropwise addition of aqueous 0.01 g sodium borohydride in 100 mL water. After addition of all the reagents, the reaction mixture was stirred for another hour.

The monometallic silver nanoparticle composition of Sample 1-1 (having Miramistin® but lacking metallic gold) was obtained using a process known in the art and was used as a control.

Table 1 shows the silver-gold molar percentages of the preparations that were obtained.

TABLE 1

| Sample No. | Au molar % in Sample |
| --- | --- |
| Sample 1-1 | 0 |
| Sample 1-2 | 0.33 |
| Sample 1-3 | 0.50 |
| Sample 1-4 | 2.50 |

Example 2

Nanoparticle Characterization—Bimetallic Nanoparticle Composition Having Miramistin®

Figure 2:
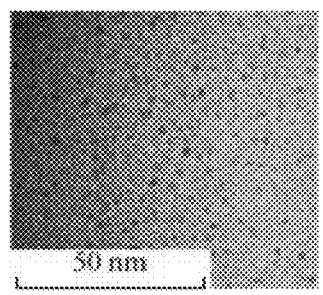
FIG. 2 is an electron micrograph of silver-gold bimetallic nanoparticles from Sample 1-3.
Figure 3:
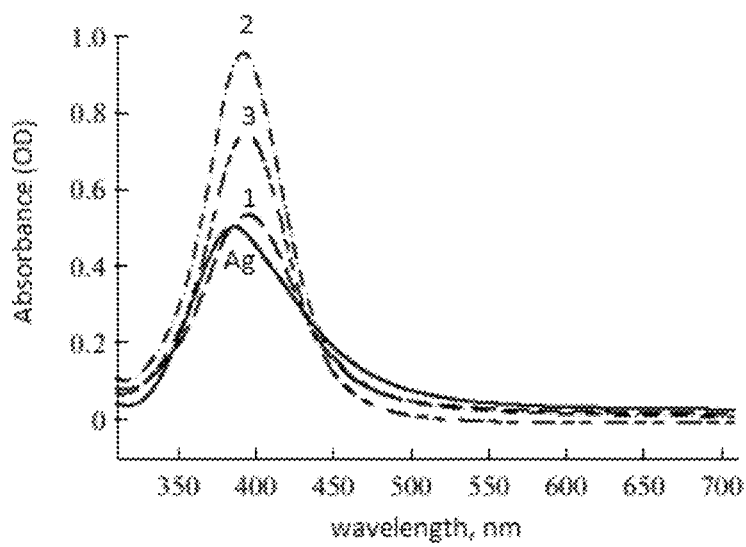
FIG. 3 shows the absorbance spectra of the nanoparticles of Example 1, wherein Sample 1-1 is represented as "Ag," Sample 1-2 is represented as "1," Sample 1-3 is represented as "2," and Sample 1-4 is represented as "3."

UV-V is absorption spectra were measured to confirm nanoparticle formation. FIG. 3 shows the absorption spectra of the nanoparticles in the resulting compositions. Incorporation of gold affects the dispersity of nanoparticles in the final product, the absorption spectra of bimetallic particles displayed more intense, narrow and symmetrical absorption bands. At 0.5% gold molar content, the nanoparticles of Sample 1-3 had the least dispersity. The dispersity difference between Samples 1-1 and 1-3 is clearly seen in FIG. 1 (Sample 1-1) and FIG. 2 (Sample 1-3).

Figure 4:
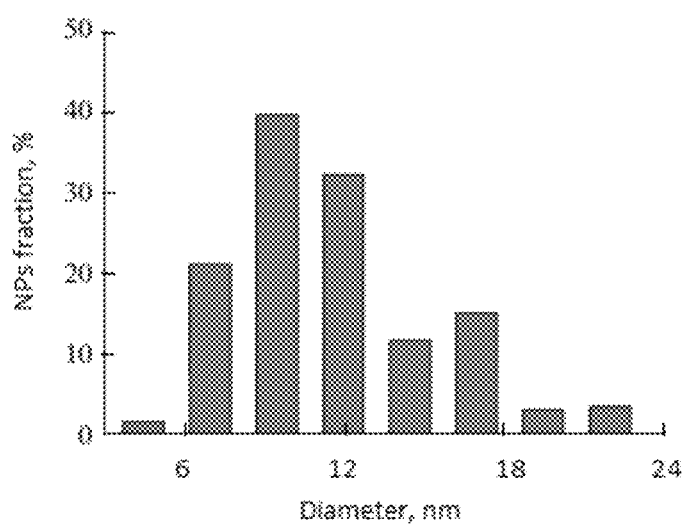
FIG. 4 shows the size distribution of the silver monometallic nanoparticles of Sample 1-1.
Figure 5:
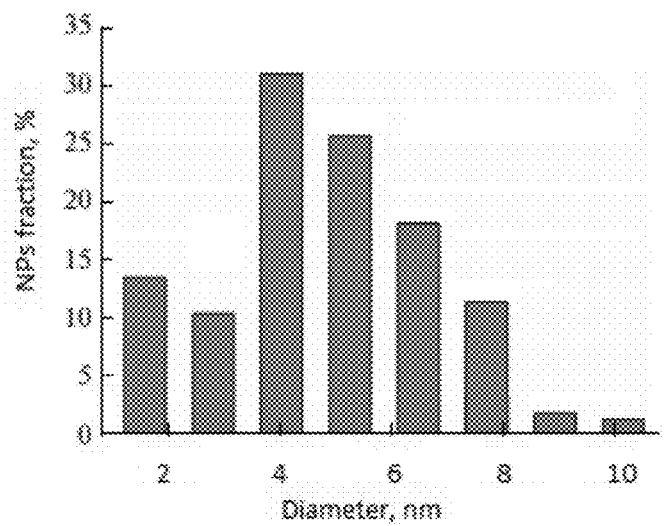
FIG. 5 shows the size distribution of the silver-gold bimetallic nanoparticles of Sample 1-3.

For a more accurate estimation of the nanoparticle size distribution of silver particle sizes versus bimetallic nanoparticles, dynamic light scattering was applied. The average diameter of silver monometallic nanoparticles (Sample 1-1) was 9-10 nm (FIG. 4), while the bimetallic nanoparticles of Sample 1-3 were smaller at 5-6 nm (FIG. 5).

Example 3

Antimicrobial and Cytotoxic Properties—Bimetallic Nanoparticle Composition with Miramistin®

Minimum inhibitory concentration (MIC) was determined to assess antibacterial and antifungal activities of the samples in microorganisms. MIC is the lowest concentration of a drug, which prevents visible growth of bacterium. The tested panel of microorganisms represent a very broad spectrum of microorganisms, including Gram-positive and Gram-negative strains (*Staphylococcus aureus* vs. *Escherichia coli*), methicillin resistant strain INA 00761 (*Staphylococcus aureus*), vancomycin resistant strain VKPM B-4177 (*Leuconostoc mesenteroides*), fungi strain INA 00760 (*Aspergillus niger*), and yeast strain RIA259 (*Saccharomyces cerevisiae*). The results obtained are presented in Table 2.

TABLE 2

| Microorganism | Silver Nitrate | Miramistin ® | Sample 1-1 | Sample 1-3 |
| --- | --- | --- | --- | --- |
| | | MIC, ug/mL | | |
| *Escherichia coli* ATCC 25922 | 10 | 20 | 1 | 0.5 |
| *Staphylococcus aureus* FDA 209P | 20 | 5 | 5 | 1 |
| *Leuconostoc mesenteroides* VKPMB-4177 | 5 | 10 | 5 | 5 |
| *Staphylococcus aureus* INA 00761 | 5 | 10 | 2.5 | 0.5 |
| *Saccharomyces cerevisiae* RIA 259 | 10 | 20 | 5 | 2.5 |
| *Aspergillus niger* INA 00760 | 20 | 20 | 5 | 0.5 |

As seen in the Table 2, the MIC of Sample 1-3 was significantly lower compared to Miramistin®, silver nitrate, and a silver monometallic nanoparticle composition with Miramistin®. Which means that silver-gold bimetallic nanoparticles with Miramistin® (Sample 1-3) are synergistically more effective against the microorganisms listed compared to the controls.

The cytotoxic effects of Samples 1-1 and 1-3 on cancer cells were studied in HCT-116 (human colon cancer cell lines), CRL-2945 (human ovarian carcinoma) and U-87 (human glioblastoma). Cell viability was analyzed in cells treated with different concentrations of Sample 1-1 and Sample 1-3. Nanoparticle samples were able to reduce viability in a dose-dependent manner. Viability was reduced significantly after 24 h of treatment. The doses were used to calculate $IC_{50}$ value against the control cells (Table 3).

TABLE 3

| Cancer cell line | IC$_{50}$, ug/mL | |
|---|---|---|
| | Sample 1-1 | Sample 1-3 |
| HCT-116 | 20 | 10 |
| CRL-2945 | 20 | 10 |
| U-87 | 15 | 5 |

As seen in the Table 3 the IC$_{50}$ of Sample 1-3 was lower compared to monometallic silver nanoparticle composition with Miramistin® (Sample 1-1). Thus, at least the silver-gold nanoparticle composition with Miramistin® of Sample 1-3 was more toxic to cancer cells compared to silver monometallic nanoparticles with Miramistin®.

Example 4

Nanoparticle Preparation—Bimetallic Silver-Gold Nanoparticle Composition with Miramistin® and Higher Gold Content The silver-gold bimetallic nanoparticle compositions of Table 4 were prepared according to the process of Example 1, wherein different amounts of gold- and silver-bearing reagents were utilized. The monometallic gold nanoparticle composition of Sample 2-4, lacking silver, was prepared according to the process of Example 1, with the exception that silver salts were omitted.

TABLE 4

| Sample No. | Au molar % in Sample |
|---|---|
| Sample 2-1 | 30 |
| Sample 2-2 | 50 |
| Sample 2-3 | 70 |
| Sample 2-4 | 100 |

Determination of the resulting nanoparticles size distribution was carried out analogously to Example 2. The average diameter of nanoparticles increased (15-20 nm). The dispersity of the colloids was also changed (data not shown).

Evaluation of antibacterial activity was carried out analogously to Example 3. The antibacterial activity of Samples 2-1 and 2-2 was higher than Samples 2-3 and 2-4. Overall, all the samples of the present example revealed less antimicrobial activity compared to the samples of Example 1 (see Table 5).

TABLE 5

| Microorganism | Sample 2-1 | Sample 2-2 | Sample 2-3 | Sample 2-4 |
|---|---|---|---|---|
| | MIC, ug/mL | | | |
| Escherichia coli ATCC 25922 | 10 | 50 | 50 | 70 |
| Staphylococcus aureus FDA 209P | 20 | 25 | 25 | 20 |
| Leuconostoc mesenteroides VKPMB-4177 | 5 | 10 | 35 | 35 |
| Staphylococcus aureus INA 00761 | 5 | 25 | 35 | 25 |
| Saccharomyces cerevisiae RIA 259 | 10 | 20 | 35 | 70 |
| Aspergillus niger INA 00760 | 20 | 25 | 25 | 20 |

Example 5

Nanoparticle Preparation—Bimetallic Silver-Gold Nanoparticle Composition with Substitution of Miramistin®

Nanoparticle compositions were prepared analogously to Sample 1-3, wherein the surfactant benzyl-dimethyl-[3-(tetradecanoylamino)propyl]ammonium chloride (Miramistin®) was substituted with cetyltrimethylammonium chloride (Sample 3-1), benzalkonium chloride (Sample 3-2), didecyldimethylammonium chloride (Sample 3-3), octenidine dihydrochloride (Sample 3-4), dimethyl benzyl ammonium chloride (Sample 3-5), and polyhexamethylene biguanide chloride (Sample 3-6).

Determination of the resulting nanoparticles size distribution was carried out analogously to Example 2. The average diameter of nanoparticles ranged from 5 to 30 nm (data not shown).

Evaluation of antibacterial activity was carried out analogously to Example 3. The antibacterial activity of the resulting products exceeded the antibacterial activity of Sample 1-1 against a series of bacteria.

TABLE 6

| Microorganism | Sample 3-1 | Sample 3-2 | Sample 3-3 | Sample 3-4 | Sample 3-5 | Sample 3-6 |
|---|---|---|---|---|---|---|
| | MIC, ug/mL | | | | | |
| Escherichia coli ATCC 25922 | — | 1 | — | — | 0.5 | — |
| Staphylococcus aureus FDA 209P | 5 | 1 | — | 20 | 30 | 1 |
| Leuconostoc mesenteroides VKPMB-4177 | — | — | 5 | — | — | — |
| Staphylococcus aureus INA 00761 | 5 | 1 | — | 2.5 | — | 0.5 |
| Saccharomyces cerevisiae RIA 259 | 2.5 | — | 2.5 | — | 10 | 2.5 |
| Aspergillus niger INA 00760 | 2.5 | — | — | — | 5 | — |

Example 6

Nanoparticle Preparation—Nanoparticle Composition with Miramistin® and Antibiotic Nanoparticle compositions with silver, Miramistin®, and an antibiotic were prepared by method A or B. Method A: aqueous solution of a silver salt was added to a solution of at least one surfactant and antibiotic under vigorous stirring, then a reducing agent was added. The reaction was carried out in an inert atmosphere of nitrogen or argon. Method B: aqueous solution of a silver salt was added to a solution of at least one surfactant under vigorous stirring, then a reducing agent was added. Upon completion of the reaction at least one antibiotic was added, and the resulting mixture stirred further. Silver nitrate or silver acetate can be used as the silver salt in both methods.

Monometallic silver nanoparticle compositions with Miramistin® and tetracycline were prepared by Method A. In more detail, distilled water was repeatedly distilled in the atmosphere of nitrogen gas to achieve de-oxygenation. The de-oxygenized water was used for all further preparations. An aqueous solution of silver nitrate (20 mg in 10 mL water) was added dropwise to vigorously stirred 150 mL 0.01 w/v % benzyl-dimethyl-[3-(tetradecanoylamino)propyl]ammonium chloride (Miramistin®) and 100 uM tetracycline in water. The resulting mixture was stirred for 15 min, followed by dropwise addition of 0.01 g sodium borohydride in 100 mL water. After addition of all the reagents the reaction mixture was stirred for another hour. The preparation steps were carried out in nitrogen or argon.

Bimetallic silver-gold nanoparticle compositions with Miramistin® and amoxicillin were prepared by Method A. In more detail, distilled water was repeatedly distilled in the atmosphere of nitrogen gas to achieve de-oxygenation. The de-oxygenized water was used for all further preparations. Solutions of 20 mg silver nitrate and 0.15 mg hydrogen tetrachloroaurate in 10 mL water were added dropwise to vigorously stirred 150 mL 0.01 w/v % benzyl-dimethyl-[3-(tetradecanoylamino)propyl]ammonium chloride (Miramistin®) and 0.1 mg/mL amoxicillin in water. The resulting mixture was stirred for 15 min, followed by dropwise addition of 0.01 g sodium borohydride in 100 mL water. After addition of all the reagents the reaction mixture was stirred for another hour. The preparation steps were carried out in nitrogen or argon.

Monometallic silver nanoparticle compositions with Miramistin and vancomycin were prepared by Method B. In more detail, 10 mL aqueous solution of 20 mg silver nitrate was added dropwise to vigorously stirred 150 mL 0.01 w/v % benzyl-dimethyl-[3-(tetradecanoylamino)propyl]ammonium chloride (Miramistin®) in water. The resulting mixture was stirred for 15 min, followed by dropwise addition of 0.01 g sodium borohydride in 100 mL water. After addition of all the reagents, the reaction mixture was stirred for another hour. Then, 10 mL of 5 uM vancomycin water solution was added to the mixture and stirred for 10 h.

Table 7 shows the abbreviations used for obtained formulations.

TABLE 7

| Sample No. | Composition |
|---|---|
| Sample 4-1 | Ag NPs - Miramistin - tetracycline |
| Sample 4-2 | Ag—Au NPs - Miramistin - amoxicillin |
| Sample 4-3 | Ag NPs - Miramistin- vancomycin |

Example 7

Figure 7:
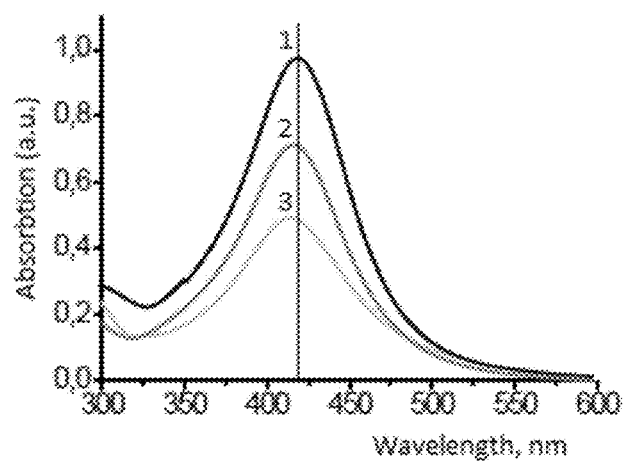
FIG. 7 shows the absorbance spectra of the nanoparticles of Example 6, wherein Sample 4-1 is represented as "2," Sample 4-2 is represented as "1," and Sample 4-3 is represented as "3."

Nanoparticle Characterization—Nanoparticle Composition with Miramistin® and Antibiotic Nanoparticle compositions formed according to Example 6 were characterized. UV-V absorption spectra were measured to confirm nanoparticle formation. FIG. 7 shows the absorption spectra of the resulting compositions. All three compositions showed typical UV absorption spectra for nanoparticles containing silver. Incorporation of gold (Sample 4-2) affects the dispersity of the nanoparticles in the final product, and the absorption spectrum of the bimetallic nanoparticles displayed a more intense, narrow, and symmetrical absorption band. TEM observations confirmed the formation of nanoparticles in all 3 samples. Confirmation of association between the nanoparticles and antibiotics was done based on Raman spectra of the nanoparticles. Raman spectra of washed and dried Samples 4-1 through 4-3 showed signals characteristic of tetracycline, amoxicillin and/or vancomycin thus demonstrating the association of the antibiotics with the nanoparticles (data not shown).

Figure 8A:
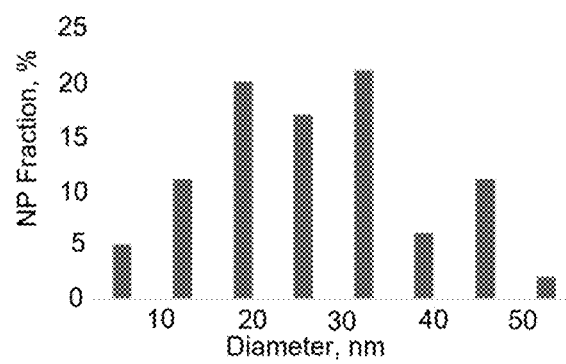
Figure 8B:
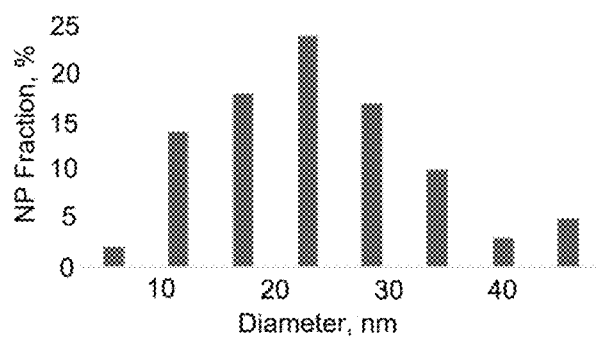
Figure 8C:
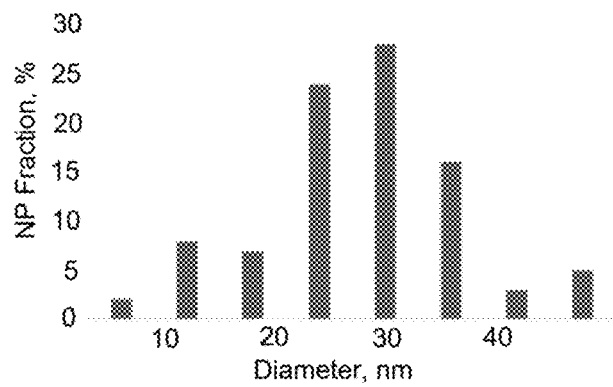

For a more accurate estimation of size distribution of the silver and silver-gold nanoparticles, dynamic light scattering was applied. The results obtained showed the average diameter of Sample 4-1 was 25 nm (FIG. 8A), Sample 4-2 was smaller at 19 nm (FIG. 8B), and Sample 4-3 was 30 nm (FIG. 8C).

Example 8

Antimicrobial Properties—Nanoparticle Composition with Miramistin® and Antibiotic Minimum inhibitory concentration (MIC) was determined to assess the antibacterial potential of the compositions of Example 6 in microorganisms. MIC is the lowest concentration of a drug which prevents visible growth of bacterium. The tested panel of microorganisms represented a very broad spectrum of antibiotic resistant microorganisms. Sample 4-1 and Tetracycline (as control) were tested against multidrug-resistant Salmonella typhimurium DT 104. Sample 4-2 and Amoxicillin (as control) were tested against Bacillus subtilis. Sample 4-3 and Vancomycin (as control) were tested against vancomycin resistant Enterococcus type Van-A and also vancomycin resistant *Leuconostoc mesenteroides* VKPM B-4177. In all test conditions monometallic silver nanoparticle composition with Miramistin® alone (obtained using a process known in the art) were used as a control. This composition is referred to as "Ag-NPs-Myramistin in Table 8. The results obtained are presented in Table 8.

TABLE 8

| Microorganism | Sample 4-1 | Tetracycline | Sample 4-2 | Amoxicillin MIC, ug/mL | Sample 4-3 | Vancomycin | Ag-NPs-Myramistin |
|---|---|---|---|---|---|---|---|
| *Salmonella typhimurium* DT 104 | 4 | >128 | — | — | — | — | 10 |
| *Bacillus subtilis* | — | — | 15 | >128 | — | — | 30 |

TABLE 8-continued

| Microorganism | Sample 4-1 | Tetracycline | Sample 4-2 | Amoxicillin | Sample 4-3 | Vancomycin | Ag-NPs-Myramistin |
|---|---|---|---|---|---|---|---|
| | | | | MIC, ug/mL | | | |
| Leuconostoc mesenteroides VKPMB-4177 | — | — | — | — | 1 | >128 | 5 |
| E. faecium A | — | — | — | — | 2 | >128 | 15 |
| E. faecalis A | — | — | — | — | 4 | >128 | 15 |

As seen in Table 8, the MIC values of nanoparticle compositions with a surfactant and an antibiotic (Samples 4-1 through 4-3) are significantly lower compared to their corresponding antibiotics applied alone. Moreover, the antibiotics showed no efficacy against drug resistant pathogens. Although the silver nanoparticle preparation with Myramistin showed antimicrobial activity, the nanoparticle compositions with Miramistin® showed a synergistic efficacy when combined with antibiotics (Samples 4-1, 4-2, and 4-3). The results demonstrate that silver Miramistin® coupled with surfactants and antibiotics not only cope with drug-resistance, but also have very high antibacterial activity.

Example 9

Nanoparticle Preparation—Monometallic Silver Nanoparticle Composition with Antibiotic and Substitution of Miramistin®

Nanoparticle compositions were prepared analogously as for Sample 4-1, wherein the surfactant benzyl-dimethyl-[3-(tetradecanoylamino)propyl]ammonium chloride (Miramistin®) was substituted with cetyltrimethylammonium chloride (Sample 5-1), benzalkonium chloride (Sample 5-2), didecyldimethylammonium chloride (Sample 5-3), octenidine dihydrochloride (Sample 5-4), dimethyl benzyl ammonium chloride (Sample 5-5), and polyhexamethylene biguanide chloride (Sample 5-6).

Determination of the resulting nanoparticle size distribution was carried out analogously to Example 2. The average diameter of the nanoparticles ranged from 10 to 50 nm (data not shown).

Evaluation of antibacterial activity was carried out analogously to Example 3. The antibacterial activity of the resulting nanoparticle compositions exceeded the antibacterial activity of silver colloid Ag-NPs-Myramistin against a series of bacteria.

TABLE 9

| Microorganism | Sample 5-1 | Sample 5-2 | Sample 5-3 | Sample 5-4 | Sample 5-5 | Sample 5-6 |
|---|---|---|---|---|---|---|
| | | | MIC, ug/mL | | | |
| Escherichia coli ATCC 25922 | 10 | 0.5 | 5 | 10 | 1 | 1 |
| Staphylococcus aureus FDA 209P | 20 | 5 | 10 | — | — | 1 |
| Leuconostoc mesenteroides VKPMB-4177 | 10 | 10 | 20 | 5 | 10 | 5 |
| Staphylococcus aureus INA 00761 | — | — | — | 10 | 10 | 1 |

TABLE 9-continued

| Microorganism | Sample 5-1 | Sample 5-2 | Sample 5-3 | Sample 5-4 | Sample 5-5 | Sample 5-6 |
|---|---|---|---|---|---|---|
| | | | MIC, ug/mL | | | |
| Saccharomyces cerevisiae RIA 259 | — | — | — | 5 | 2.5 | 5 |
| Aspergillus niger INA 00760 | 5 | 2.5 | 20 | — | — | — |

Example 10

Nanoparticle Preparation—Monometallic Platinum Nanoparticle Composition with Miramistin® and Glucosamine or Doxorubicin Monometallic platinum nanoparticle compositions comprising Miramistin® and glucosamine or doxorubicin were prepared as follows: aqueous solution of 50 mg hexachloroplatinic acid hexahydrate in 10 mL water was added dropwise to vigorously stirred aqueous 150 mL 0.01 w/v % benzyl-dimethyl-[3-(tetradecanoylamino)propyl]ammonium chloride (Miramistin®). The resulting mixture was stirred for 15 min, followed by dropwise addition of 0.01 g sodium borohydride in 100 mL water. The color changed to dark brown. After addition of all the reagents, the reaction mixture was stirred for another hour. Then glucosamine (Sample 6-1) or a doxorubicin water solution (Sample 6-2) was added, and the resulting mixture stirred further.

Table 10 shows the abbreviations used for the nanoparticle compositions obtained.

TABLE 10

| Sample No. | Composition |
|---|---|
| Sample 6-1 | Pt NPs - Miramistin - Glucosamine |
| Sample 6-2 | Pt NPs - Miramistin - Doxorubicin |

Example 11

Nanoparticle Preparation—Bimetallic Silver Nanoparticle Composition with Miramistin® and Doxorubicin or Metformin A bimetallic silver-platinum nanoparticle composition with Miramistin® and Metformin was prepared as follows: aqueous solution of silver nitrate (20 mg in 10 mL water) was added dropwise to vigorously stirred 0.01 w/v % benzyl-dimethyl-[3-(tetradecanoylamino)propyl]ammonium chloride (Miramistin®). The resulting mixture was stirred for 15 min, followed by dropwise addition of 100 mL aqueous 0.01 g sodium borohydride. The color changed to brown. 2.5 mg hexachloroplatinic acid hexahydrate in 10 mL water was added dropwise to the resulting reaction mixture, stirred for 1 h, followed by dropwise addition of 10 mL aqueous 1 mg sodium borohydride. After addition of all the reagents, the reaction mixture was stirred for another hour. Then a Metformin water solution was added, and the resulting mixture stirred further.

A bimetallic silver-gold nanoparticle composition with Miramistin and Doxorubicin was prepared by Method A described in Example 6. In more detail, distilled water was repeatedly distilled in the atmosphere of nitrogen gas to achieve de-oxygenation. The de-oxygenized water was used for all further preparations. Aqueous solutions of 20 mg silver nitrate and 0.15 mg hydrogen tetrachloroaurate were added dropwise to vigorously stirred 150 mL 0.01 w/v % benzyl-dimethyl-[3-(tetradecanoylamino)propyl]ammonium chloride (Miramistin) in water. The resulting mixture was stirred for 15 min, followed by dropwise addition of 0.01 g sodium borohydride in 100 mL water. After addition of all the reagents the reaction mixture was stirred for another hour. Then a Doxorubicin water solution was added, and the resulting mixture stirred further. Table 11 shows the abbreviations used for the obtained compositions.

TABLE 11

| Sample No. | Composition |
|---|---|
| Sample 7-1 | Pt—Ag NPs - Miramistin - Metformin |
| Sample 7-2 | Au—Ag NPs - Miramistin - Doxorubicin |

Example 12

Nanoparticle Characterization—Platinum Nanoparticles

Figure 9:
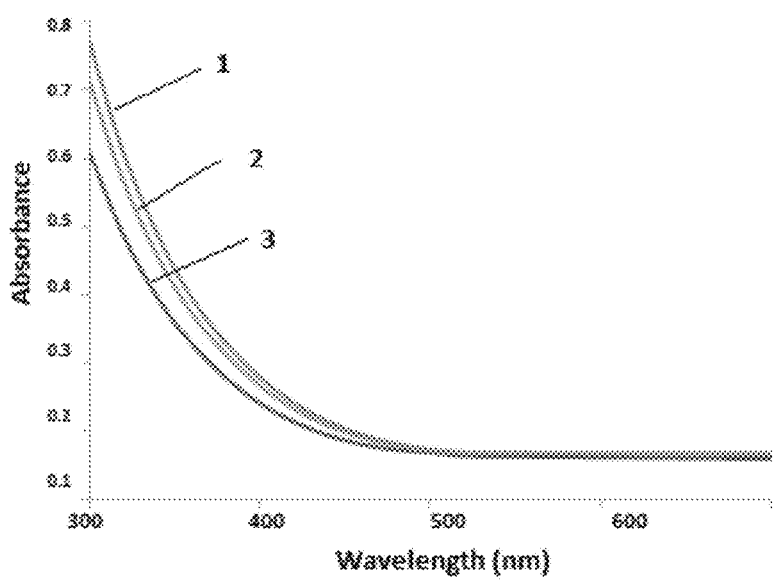
FIG. 9 shows the absorbance spectra of the nanoparticles of Examples 10 and 11, wherein Sample 6-1 is represented as "3," Sample 6-2 is represented as "1," and Sample 7-1 is represented as "2."
Figure 10A:
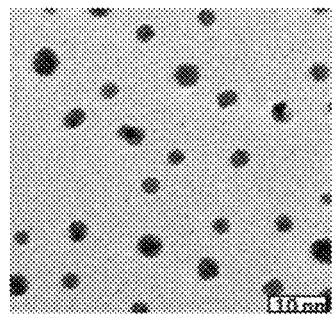
Figure 10B:
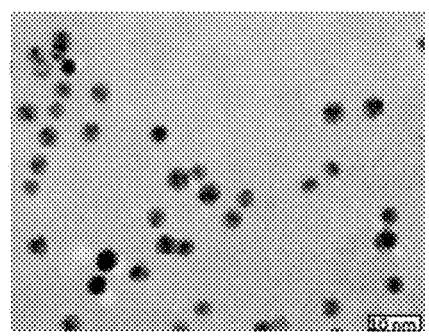
Figure 10C:
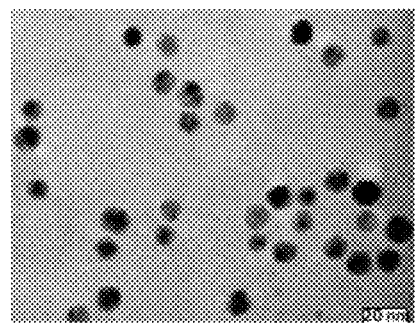
Figure 11A:
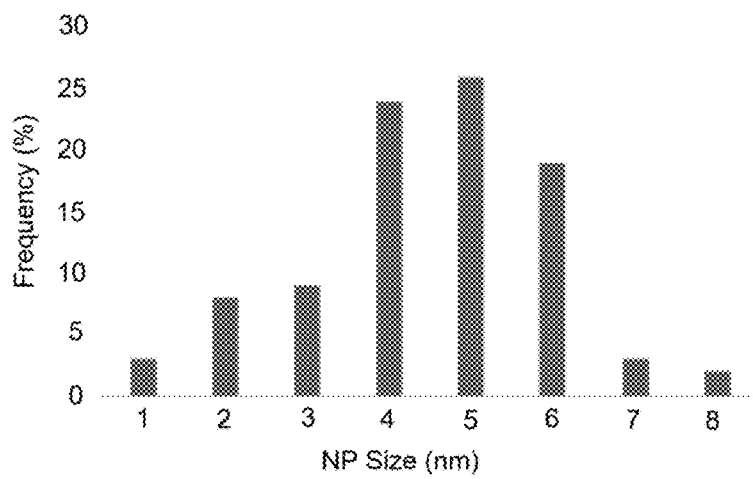
Figure 11B:
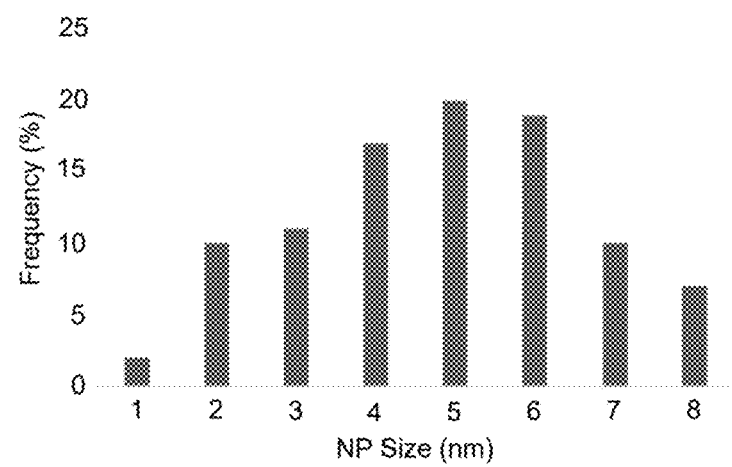
Figure 11C:
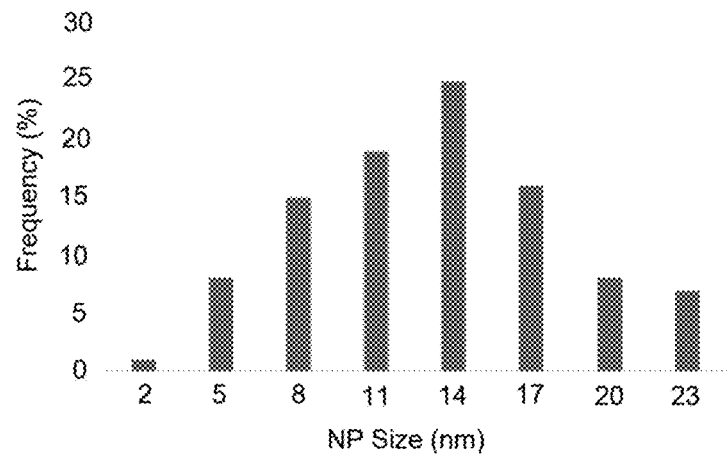

UV-Vis absorption spectra were measured to confirm formation of the nanoparticles in the compositions of Examples 10 and 11. FIG. 9 shows the absorption spectra of the resulting nanoparticles. All 4 nanoparticles showed UV absorption spectra typical for platinum nanoparticles. Incorporation of silver (Sample 7-1) resulted in a red shift in the UV spectrum. TEM observations confirmed the formation of nanoparticles in all 4 samples (FIGS. 10A-10C). The confirmation of doxorubicin associated with the nanoparticles was done based on Raman spectra. Raman spectra of washed and dried Samples 6-2 and 7-2 showed signals characteristic of doxorubicin (data not shown). For a more accurate estimation of the nanoparticle size distribution, dynamic light scattering was applied. The average diameter of Sample 6-1 was 4.5 nm (FIG. 11A), Sample 6-2 was slightly smaller at 4 nm (FIG. 11B), Sample 7-1 was 3 times bigger at 13 nm (FIG. 11C), and Sample 7-2 was around 5 nm (data not shown).

Example 13

Anticancer Properties—Platinum and Silver Containing Nanoparticle Compositions with Miramistin® and Drug The cytotoxic effects of Samples 6-1, 6-2, 7-1 and 7-2, glucosamine and Metformin on cancer cells were studied in CRL-2945 (human ovarian carcinoma) and U-87 (human glioblastoma). The doxorubicin resistant CRL-2945 and U-87 cells were generated by exposing the cells to the cytotoxic drug at incrementally increasing concentrations. In this way, resistant sublines were obtained (CRL-2945-R and U-87-R). The cell viability was analyzed in cells treated with different concentrations of Sample 6-1, Sample 6-2, Sample 7-1 and Sample 7-2. The samples were able to reduce viability in a dose-dependent manner. Viability reduced significantly after 24 h of treatment. The doses were used to calculate $IC_{50}$ values against the control cells (Table 12).

TABLE 12

| | $IC_{50}$ | | | | |
|---|---|---|---|---|---|
| Cancer cell line | Doxorubicin, uM | Sample, 6-1 ug/mL | Sample 6-2, ug/mL | Sample 7-1, ug/mL | Sample 7-2, ug/mL |
| CRL-2945 | 0.13 | 40 | 5 | 20 | 25 |
| U-87 | 0.08 | 20 | 2 | 10 | 20 |
| CRL-2945 -R | 0.28 | 40 | 7 | 20 | 30 |
| U-87 -R | 1.2 | 15 | 8 | 10 | 20 |

As seen in the Table 12 the $IC_{50}$ of Sample 6-2 is the lowest compared to the other compositions tested. Higher toxicity of Sample 6-2 can be explained by the fact that Sample 6-2 bears very toxic doxorubicin, which is delivered into the cells with nanoparticles. Doxorubicin resistant cell sublines were significantly less resistant to nanoparticles with doxorubicin (i.e. Sample 6-2). Sample 6-1 and Sample 7-1 showed high cell toxicity at higher concentrations, but affected the amount of cancer stem cells (CSCs) as seen in Table 13. Cancer cells CRL-2945-R and U-87-R were cultured in serum-free media to enrich the populations with cancer stem cells. Thus, enriched cells were tested with the samples. Glucosamine and Metformin alone did not show any significant activity (data not shown).

TABLE 13

| | Before treatment with NPs | | After treatment with Sample 6-1, 40 ug/mL | | After treatment with Sample 7-1, 20 ug/mL | |
|---|---|---|---|---|---|---|
| Cancer cell line | CD44, % positive cells | CD24, % positive cells | CD44, % positive cells | CD24, % positive cells | CD44, % positive cells | CD24, % positive cells |
| CRL-2945 | 20 | 23 | 12 | 50 | 7 | 58 |
| U-87 | 55 | 20 | 42 | 45 | 33 | 56 |

As seen in the Table 13 the percentage of CSC (CD44 high, CD24 low) decreased after treatment of the cells with Sample 6-1 and 7-1. Sample 7-1 had a more prominent effect.

Example 14

Nanoparticle Preparation—Monometallic Platinum Nanoparticle Composition with Doxorubicin and Substitution of Miramistin®

Nanoparticle compositions were prepared analogously to Sample 6-2, wherein the surfactant benzyl-dimethyl-[3-(tetradecanoylamino)propyl]ammonium chloride (Miramistin®) was substituted with cetyltrimethylammonium chloride (Sample 8-1), benzalkonium chloride (Sample 8-2), didecyldimethylammonium chloride (Sample 8-3), octenidine dihydrochloride (Sample 8-4), dimethyl benzyl ammonium chloride (Sample 8-5), and polyhexamethylene biguanide chloride (Sample 8-6).

Determination of the resulting nanoparticle size distribution was carried out analogously to Example 12. The average diameter of nanoparticles ranged from 5 to 45 nm (data not shown).

Evaluation of anticancer activity was carried out analogously to Example 13. The anticancer activity of the resulting products is also high and similar concentration ranges.

TABLE 14

| Cancer cell line | $IC_{50}$ | | | | | |
|---|---|---|---|---|---|---|
| | Sample 8-1 | Sample 8-2 | Sample 8-3 | Sample 8-4 | Sample 8-5 | Sample 8-6 |
| CRL-2945 | 25 | 15 | 20 | 20 | 20 | 10 |
| U-87 | 10 | 20 | 20 | 15 | 15 | 5 |
| CRL-2945 -R | 20 | 10 | 25 | 20 | 25 | 10 |
| U-87 -R | 10 | 15 | 20 | 20 | 10 | 5 |

Table 15 presents the various embodiments of the nanoparticles exemplified above, including their corresponding examples.

TABLE 15

| Sample No. | Composition | Relevant Examples |
|---|---|---|
| Sample 1-1 | Monometallic silver nanoparticles with Miramistin ® | Examples 1, 2, 3, and 5 |
| Sample 1-2 | Bimetallic silver-gold nanoparticles with Miramistin ®; 99.67% molar Ag to 0.33% molar Au | Examples 1 and 2 |
| Sample 1-3 | Bimetallic silver-gold nanoparticles with Miramistin ®; 99.50% molar Ag to 0.50% molar Au | Examples 1, 2, 3, and 4 |
| Sample 1-4 | Bimetallic silver-gold nanoparticles with Miramistin ®; 97.50% molar Ag to 2.50% molar Au | Example 1 |
| Sample 2-1 | Bimetallic silver-gold nanoparticles with Miramistin ®; 70% molar Ag to 30% molar Au | Example 4 |
| Sample 2-2 | Bimetallic silver-gold nanoparticles with Miramistin ®; 50% molar Ag to 50% molar Au | Example 4 |
| Sample 2-3 | Bimetallic silver-gold nanoparticles with Miramistin ®; 30% molar Ag to 70% molar Au | Example 4 |
| Sample 2-4 | Monometallic gold nanoparticles with Miramistin ® | Example 4 |
| Sample 3-1 | Bimetallic silver-gold nanoparticles with cetyltrimethylammonium chloride; 99.50% molar Ag to 0.50% molar Au | Example 5 |
| Sample 3-2 | Bimetallic silver-gold nanoparticles with benzalkonium chloride; 99.50% molar Ag to 0.50% molar Au | Example 5 |
| Sample 3-3 | Bimetallic silver-gold nanoparticles with didecyldimethylammonium chloride; 99.50% molar Ag to 0.50% molar Au | Example 5 |
| Sample 3-4 | Bimetallic silver-gold nanoparticles with octenidine dihydrochloride; 99.50% molar Ag to 0.50% molar Au | Example 5 |
| Sample 3-5 | Bimetallic silver-gold nanoparticles with dimethyl benzyl ammonium chloride; 99.50% molar Ag to 0.50% molar Au | Example 5 |
| Sample 3-6 | Bimetallic silver-gold nanoparticles with polyhexamethylene biguanide chloride; 99.50% molar Ag to 0.50% molar Au | Example 5 |
| Sample 4-1 | Monometallic silver nanoparticles with Miramistin ® and tetracycline | Examples 6, 7, and 8 |
| Sample 4-2 | Bimetallic silver-gold nanoparticles with Miramistin ® and amoxicillin | Examples 6, 7, and 8 |
| Sample 4-3 | Monometallic silver nanoparticles with Miramistin ® and vancomycin | Examples 6, 7, and 8 |
| Sample 5-1 | Monometallic silver nanoparticles with cetyltrimethylammonium chloride and tetracycline | Example 9 |
| Sample 5-2 | Monometallic silver nanoparticles with benzalkonium chloride and tetracycline | Example 9 |
| Sample 5-3 | Monometallic silver nanoparticles with didecyldimethylammonium chloride and tetracycline | Example 9 |
| Sample 5-4 | Monometallic silver nanoparticles with octenidine dihydrochloride and tetracycline | Example 9 |
| Sample 5-5 | Monometallic silver nanoparticles with dimethyl benzyl ammonium chloride and tetracycline | Example 9 |
| Sample 5-6 | Monometallic silver nanoparticles with polyhexamethylene biguanide chloride and tetracycline | Example 9 |
| Sample 6-1 | Monometallic platinum nanoparticles with Miramistin ® and glucosamine | Examples 10, 12, and 13 |
| Sample 6-2 | Monometallic platinum nanoparticles with Miramistin ® and doxorubicin | Examples 10, 12, and 13 |
| Sample 7-1 | Bimetallic silver-platinum nanoparticles with Miramistin ® and metformin | Examples 11, 12, and 13 |
| Sample 7-2 | Bimetallic silver-gold nanoparticles with Miramistin ® and doxorubicin | Examples 11, 12, and 13 |
| Sample 8-1 | Monometallic platinum nanoparticles with cetyltrimethylammonium chloride and glucosamine | Example 14 |
| Sample 8-2 | Monometallic platinum nanoparticles with benzalkonium chloride and glucosamine | Example 14 |
| Sample 8-3 | Monometallic platinum nanoparticles with didecyldimethylammonium chloride and glucosamine | Example 14 |
| Sample 8-4 | Monometallic platinum nanoparticles with octenidine dihydrochloride and glucosamine | Example 14 |
| Sample 8-5 | Monometallic platinum nanoparticles with dimethyl benzyl ammonium chloride and glucosamine | Example 14 |
| Sample 8-6 | Monometallic platinum nanoparticles with polyhexamethylene biguanide chloride and glucosamine | Example 14 |

REFERENCES

1. A. D. Russell, W. Hugo, Prog. Med. Chem. 31 (1994) 351-370
2. K. Dunn, V. Edwards-Jones, Burns 30 (2004) 1-9
3. M. Ip, S. L. Lui, V. K. Poon, I. Lung, et al, J. Med. Microbiol 55 (2006) 59-63
4. M. Rai, S. Yadav, A. Gade, Biotechnol. Adv. 27 (2009) 76-83
5. J. L. Elechiguerra, J. L. Burt, J. R. Morones, A. Camacho-Bragado, et al, J. Nanobiotechnol. 3 (2005) 6-10
6. R. W. Sun, R. Chen, N. P. Chung, C. M. Ho, et al, Chem. Commun. (Camb.) 40 (2005) 5059-5061
7. L. Lu, R. W. Sun, R. Chen, C. K. Hui, et al, Antiviral Ther. 13 (2008) 253-262
8. L. Sun, A. K. Singh, K. Vig, S. Pillai, et al, J. Biomed. Biotechnol. 4 (2008) 149-158
9. M. I. Sriram, S. B. M. Kanth, K. Kalishwaralal, S. Gurunathan, Int. J. Nanomed. 5 (2010) 753-762
10. D. Martins, L. Frungillo, M. C. Anazzetti, P. S. Melo, et al, Int. J. Nanomed. 5 (2010) 77-85
11. Smetana A B, Klabunde K J, Marchin G R, Sorensen C M. Langmuir 24 (2008) 7457-7464
12. M. Lv, S. Su, Y. He, Q. Huang, W. Hu, D. Li, et al. Adv Mater 22 (2010) 5463-5467
13. Y. Tian, J. Qi, W. Zhang, Q. Cai, X. Jiang. ACS Appl Mater Interfaces 6 (2014) 12038-12045
14. M. K. Rai, S. D. Deshmukh, A. P. Ingle, A. K. Gade. J Appl Microbiol 112 (2012) 841-852
15. Patent RU2342120C2
16. A. Paraskar, S. Soni, et al. Nanotechnology 23(7) (2012) 075103
17. N. E. Madias, J. T. Harrington. The American journal of medicine 65(2) (1978) 307-314
18. L. Galluzzi, L. Senovilla, et al. Oncogene 31(15) (2012) 1869
19. J. Woodcock, J. P. Griffin, et al. New England Journal of Medicine 364(11) (2011)985-987

What is claimed is:

1. A composition comprising (i) particles comprising at least one metal, (ii) at least one surfactant, and (iii) at least one antibiotic.
2. The composition of claim 1, wherein said at least one metal comprises one or more metals selected from silver, gold, platinum, palladium, osmium, iridium, rhodium, and ruthenium.
3. The composition of claim 1, wherein said particles are monometallic particles, polymetallic particles, or a combination of monometallic particles and polymetallic particles.
4. The composition of claim 3, wherein said polymetallic particles include bimetallic particles.
5. The composition of claim 4, wherein said bimetallic particles comprise one or more bimetallic particles selected from silver and gold bimetallic particles, and silver and platinum bimetallic particles.
6. The composition of claim 5, wherein said composition comprises about 99.67% molar silver, about 99.50% molar silver, about 97.50% molar silver, about 70% molar silver, or about 50% molar silver.
7. The composition of claim 3, wherein said polymetallic particles have a core and at least one shell.
8. The composition of claim 7, wherein said polymetallic particles are bimetallic particles and said core includes gold or platinum and said shell includes silver.
9. The composition of claim 3, wherein said polymetallic particles comprise an alloy, a mixed alloy, subclusters with two or more interfaces, or combinations thereof.
10. The composition of claim 9, wherein said subclusters comprise one or more subclusters selected from segregated subclusters and mixed subclusters.
11. The composition of claim 9, wherein said alloy is an intermetallic alloy.
12. The composition of claim 3, wherein said monometallic particles comprise one or more monometallic particles selected from silver monometallic particles, gold monometallic particles, and platinum monometallic particles.
13. The composition of claim 1, wherein said particles include nanoparticles.
14. The composition of claim 13, wherein said nanoparticles have a mean diameter of between about 5 nanometers and about 400 nanometers, or between about 5 nanometers and about 30 nanometers.
15. The composition of claim 1, wherein said composition comprises particles having a shape selected from substantially spherical, substantially oval, substantially cuboidal, and combinations thereof.
16. The composition of claim 1, wherein said at least one surfactant comprises one or more surfactants selected from a cationic surfactant, an anionic surfactant, an amphoteric surfactant, and a charge-neutral surfactant.
17. The composition of claim 1, wherein said at least one surfactant comprises one or more surfactants selected from benzyl-dimethyl-[3-(tetradecanoylamino)propyl]ammonium chloride, a cetyltrimethylammonium salt, a benzalkonium salt, didecyldimethylammonium chloride, octenidine dihydrochloride, dimethyl benzyl ammonium chloride, a polyhexamethylene biguanide, a polyhexamethylene guanidine, a polyhexamethylene biguanide salt, a polyhexamethylene guanidine salt, sodium lauryl ether sulfate, and sodium cocaminopropionate.
18. The composition of claim 1, wherein at least a portion of said at least one surfactant is coupled to a surface of said particles.
19. The composition of claim 1, wherein said at least one antibiotic comprises an antibiotic selected from tetracycline, vancomycin, or a combination thereof.
20. The composition of claim 1, wherein at least a portion of said at least one antibiotic is coupled to a surface of said particles, said at least one surfactant, or a combination thereof.
21. The composition of claim 1, wherein said composition further comprises a drug.
22. The composition of claim 21, wherein said drug comprises one or more drugs selected from doxorubicin, glucosamine, and metformin.
23. The composition of claim 21, wherein at least a portion of said drug is coupled to a surface of said particles, said at least one surfactant, said at least one antibiotic, or a combination thereof.
24. The composition of claim 1, wherein (i) said composition further comprises at least one of a carrier and an excipient, and (ii) at least a portion of one or more of said at least one surfactant, and said at least one antibiotic is dissolved in or suspended in said carrier and/or said excipient.
25. The composition of claim 1, wherein said composition is a colloid.
26. The composition of claim 1, wherein said composition is in a form selected from a liquid, gel, sol, and foam.
27. The composition of claim 1, wherein said composition is in an administration form selected from a pill, capsule, tablet, microbead, injection, infusion, and suppository.
28. The composition of claim 1, wherein said composition is in contact with a bandage or wound dressing.

29. The composition of claim 1, wherein said composition is in contact with a textile.

30. The composition of claim 29, wherein said textile is a bed sheet, blanket, pillow, pillow case, seat cover, table cover, door mat, gauze, surgical mask, surgical gown, patient gown, menstrual pad, or tampon.

31. A composition comprising bimetallic nanoparticles comprising a metallic gold core substantially surrounded by a shell of metallic silver, wherein benzyl-dimethyl-[3-(tetradecanoylamino)propyl]ammonium chloride is coupled to a surface of said shell and amoxicillin is coupled to at least one of said surface of shell and said benzyl-dimethyl-[3-(tetradecanoylamino)propyl]ammonium chloride.

32. The nanoparticle of claim 31, wherein said composition has a molar content of gold and silver that is: about 0.33% gold and about 99.67% silver; about 0.50% gold and about 99.50% silver; about 2.50% gold and about 97.50% silver; about 30% gold and about 70% silver; about 50% gold and about 50% silver; or about 70% gold and about 30% silver.

33. A method of treating a microbial infection, comprising administering to a patient in need thereof a composition according to claim 1.

34. The method of claim 33, wherein said patient has at least one of a bacterial infection, a viral infection, and a fungal infection.

* * * * *